United States Patent
Spinelli et al.

(10) Patent No.: US 9,504,829 B2
(45) Date of Patent: Nov. 29, 2016

(54) IMPLANTABLE MEDICAL LEAD WITH COLLAPSIBLE FIXATION MEMBER

(71) Applicant: Nuvectra Corporation, Plano, TX (US)

(72) Inventors: Michele Spinelli, Milan (IT); John M. Swoyer, Blaine, MN (US)

(73) Assignee: Nuvectra Corporation, Plano, TX (US)

( * ) Notice: Subject to any disclaimer, the term of this patent is extended or adjusted under 35 U.S.C. 154(b) by 81 days.

(21) Appl. No.: 14/537,051

(22) Filed: Nov. 10, 2014

(65) Prior Publication Data

US 2015/0134038 A1  May 14, 2015

Related U.S. Application Data

(60) Provisional application No. 61/901,499, filed on Nov. 8, 2013, provisional application No. 61/923,927, filed on Jan. 6, 2014.

(51) Int. Cl.
*A61N 1/05* (2006.01)
*A61N 1/36* (2006.01)
*A61N 1/372* (2006.01)

(52) U.S. Cl.
CPC .......... *A61N 1/36132* (2013.01); *A61N 1/05* (2013.01); *A61N 1/0512* (2013.01); *A61N 1/0551* (2013.01); *A61N 1/0558* (2013.01); *A61N 1/3606* (2013.01); *A61N 1/36007* (2013.01); *A61N 1/36146* (2013.01); *A61N 1/37235* (2013.01); *A61N 1/37247* (2013.01)

(58) Field of Classification Search
CPC ...... A61N 1/36132; A61N 1/37235; A61N 1/36146; A61N 1/3606; A61N 1/05; A61N 1/37247; A61N 1/0512; A61N 1/36007; A61N 1/0058; A61N 1/0551
See application file for complete search history.

(56) References Cited

U.S. PATENT DOCUMENTS

| | | | |
|---|---|---|---|
| 6,645,205 B2 | 11/2003 | Ginn | |
| 8,277,467 B2 | 10/2012 | Copa et al. | |
| 8,409,193 B2 | 4/2013 | Young et al. | |
| 8,758,398 B2 | 6/2014 | Carley | |
| 2003/0028153 A1* | 2/2003 | Brennan | A61M 25/0662 604/263 |
| 2005/0113716 A1 | 5/2005 | Mueller et al. | |
| 2005/0288764 A1 | 12/2005 | Snow et al. | |
| 2013/0166007 A1* | 6/2013 | True | A61N 1/36 607/116 |

* cited by examiner

*Primary Examiner* — Rex R Holmes
(74) *Attorney, Agent, or Firm* — Haynes and Boone, LLP; Eric Q. Li

(57) ABSTRACT

In various examples, a stimulation lead for at least partial implantation within a patient includes an elongate lead body and a sheath selectively attachable to the lead body. The sheath includes a fixation member. The fixation member includes a retracted configuration in which the fixation member is disposed proximate the sheath. In a deployed configuration, the fixation member extends radially outwardly from the sheath to anchor the stimulation lead within the patient. In a removal configuration, the fixation member is radially inwardly collapsible toward the longitudinal sheath axis with the lead body removed from within the sheath.

20 Claims, 5 Drawing Sheets

IMPLANTABLE MEDICAL LEAD WITH COLLAPSIBLE FIXATION MEMBER

CROSS REFERENCE TO RELATED APPLICATIONS

This application claims the benefit of priority to U.S. Provisional Application Ser. No. 61/901,499, filed on Nov. 8, 2013, entitled "STIMULATION APPARATUSES, DEVICES, SYSTEMS, AND METHODS," and U.S. Provisional Application Ser. No. 61/923,927, filed on Jan. 6, 2014, entitled "STIMULATION APPARATUSES, DEVICES, SYSTEMS, AND METHODS," each of which is incorporated by reference herein in its entirety.

TECHNICAL FIELD

The present patent document pertains generally to a stimulation apparatus, system, and method and more particularly, but not by way of limitation, to an implantable apparatus, system, and method including a collapsible fixation member.

BACKGROUND

Stimulation of various nerves and tissue has been found to be a promising treatment for various conditions and/or ailments. For instance, pain, urinary urge, fecal incontinence, and epilepsy, to name a few, are indications for various nerve/tissue stimulation therapies. Various nerves and tissue are commonly targeted for stimulation therapy, including, but not limited to the sacral nerve, the pudendal nerve, the vagus nerve, the tibial nerve, and the spinal cord, to name a few.

Leads used for nerve and/or tissue stimulation often include tines for anchoring the lead within the patient. Leads with integral tines or other fixation members can be difficult to extract, should the need arise, due to the retention force that the tines or other fixation members offer. Sometimes, the retention force is so high that the physician can break the lead when pulling on it. This presents problems in that the portion of the lead, if it were to remain in the patient, could present health risks. However, if the physician tries to remove the portion of the lead, that too could present health risks in trying to access the portion of the lead and pull it out or surgically extract it. As such, while tines or other fixation members mitigate lead migration during use, they also present issues during extraction of the lead.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the present subject matter can be used to provide an implantable stimulation lead including a selectively collapsible fixation member in order to decrease removal force for removing the stimulation lead from within a patient. To better illustrate the apparatuses, systems, and methods described herein, a non-limiting list of examples is provided here:

Example 1 can include subject matter that can include a stimulation lead for at least partial implantation within a patient. The stimulation lead includes an elongate lead body including a distal end and a proximal end. A sheath is selectively attachable to the lead body and includes a longitudinal sheath axis. A lumen extends from a proximal sheath end to a distal sheath end. A fixation member is disposed on the sheath. With the sheath attached to the lead body, the lead body is disposed at least partially within the lumen of the sheath, and the lead body and the sheath are substantially coaxial. The fixation member includes a retracted configuration in which the fixation member is disposed proximate the sheath. A deployed configuration includes the fixation member extending radially outwardly from the sheath to anchor the stimulation lead within the patient. A removal configuration includes the fixation member radially inwardly collapsible toward the longitudinal sheath axis with the lead body removed from within the sheath.

In Example 2, the subject matter of Example 1 is optionally configured such that the sheath includes a plurality of fixation members.

In Example 3, the subject matter of any one of Examples 1-2 is optionally configured such that the fixation member is disposed proximate the distal sheath end.

In Example 4, the subject matter of any one of Examples 1-3 is optionally configured such that the sheath is compressively attachable to the lead body.

In Example 5, the subject matter of Example 4 is optionally configured such that the sheath includes a suture disposed around the sheath, wherein tightening of the suture compressively engages the sheath to the lead body.

In Example 6, the subject matter of any one of Examples 1-5 is optionally configured such that the sheath includes a suture groove for retaining a suture within the suture groove, wherein tightening of the suture compressively engages the sheath to the lead body.

In Example 7, the subject matter of Example 6 is optionally configured such that the suture groove is disposed around the sheath proximate a proximal end of the sheath.

In Example 8, the subject matter of any one of Examples 6-7 is optionally configured such that the sheath includes a radiopaque marker proximate the suture groove.

In Example 9, the subject matter of any one of Examples 1-8 is optionally configured such that the fixation member includes a tine.

In Example 10, the subject matter of any one of Examples 1-9 is optionally configured such that the fixation member is retained within the retracted configuration with the fixation member disposed within an introducer.

In Example 11, the subject matter of any one of Examples 1-10 is optionally configured such that the fixation member is retained in the deployed configuration with the lead body disposed within the lumen and extending from the distal end of the sheath.

In Example 12, the subject matter of any one of Examples 1-11 is optionally configured such that the fixation member is biased to the deployed configuration.

In Example 13, the subject matter of any one of Examples 1-12 is optionally configured such that the sheath includes a base on which the fixation structure is disposed, the base being deflectable with respect to the remainder of the sheath. With the lead body disposed within the sheath, the base is inhibited from deflecting. With the lead body removed from within the sheath, the base is able to deflect radially inwardly toward the longitudinal sheath axis to allow the fixation member to be radially inwardly collapsible in the removal configuration.

Example 14 can include, or can optionally be combined with any one of Examples 1-13 to include subject matter that can include an apparatus for at least partial implantation within a patient. The apparatus includes a sheath selectively attachable to the lead body. The sheath includes a longitudinal sheath axis. A lumen extends from a proximal sheath end to a distal sheath end. At least one fixation member disposed on the sheath. An elongate lead body includes a distal end and a proximal end. The lead body is sized and shaped to fit within the lumen of the sheath. With the lead body disposed within the sheath, the lead body and the sheath are substantially coaxial. The at least one fixation member includes a retracted configuration in which the at least one fixation member is disposed proximate the sheath. A deployed configuration includes the at least one fixation member extending radially outwardly from the sheath to anchor the apparatus within the patient. A removal configuration includes the at least one fixation member radially inwardly collapsible toward the longitudinal sheath axis with the lead body removed from within the sheath.

In Example 15, the subject matter of Example 14 is optionally configured such that the at least one fixation member is disposed proximate a distal end of the sheath.

In Example 16, the subject matter of any one of Examples 14-15 is optionally configured such that the sheath is compressively attachable to the lead body.

In Example 17, the subject matter of Example 16 optionally includes a suture disposed around the sheath within a suture groove proximate a proximal end of the sheath, wherein tightening of the suture compressively engages the sheath to the lead body.

In Example 18, the subject matter of any one of Examples 14-17 optionally includes an introducer removably disposed around the sheath and the at least one fixation member of the sheath. The at least one fixation member is retained within the retracted configuration with the at least one fixation member disposed within the introducer. Removal of the sheath from within the introducer allows the at least one fixation member to move to the deployed configuration.

In Example 19, the subject matter of any one of Examples 14-18 is optionally configured such that the at least one fixation member is biased to the deployed configuration.

In Example 20, the subject matter of any one of Examples 14-19 is optionally configured such that the sheath includes a base on which the at least one fixation structure is disposed. The base is deflectable with respect to the remainder of the sheath. With the lead body disposed within the sheath, the base is inhibited from deflecting. With the lead body removed from within the sheath, the base is able to deflect radially inwardly toward the longitudinal sheath axis to allow the at least one fixation member to be radially inwardly collapsible in the removal configuration.

DETAILED DESCRIPTION

The present patent document relates to apparatuses, systems, and methods for anchoring an implantable device within a patient. In some examples, the apparatuses, systems, and methods described herein relate to a stimulation lead. In some examples, the apparatuses, systems, and methods described herein relate to a stimulation lead including a collapsible fixation member.

The present inventors have recognized, among other things, that it is desirable to provide an implantable stimulation lead including a selectively collapsible fixation member in order to decrease removal force for removing the stimulation lead from within a patient. By decreasing the removal force, the present inventors have recognized, among other things, that, in some examples, fewer leads will break during removal procedures, potentially leading to decreased complications and cost associated with removal procedures. While primarily described with respect to stimulation leads, it should be understood, however, that the subject matter described herein can be used with other apparatuses, such as, but not limited to implantable medical devices.

Referring to FIGS. 1-9, in some examples, the apparatuses, devices, systems, and methods described herein can include a stimulation lead including one or more fixation members that can collapse during extraction. In this way, removal force can be decreased from that of conventional leads having deployed tines or other fixation structures.

Figure 6:
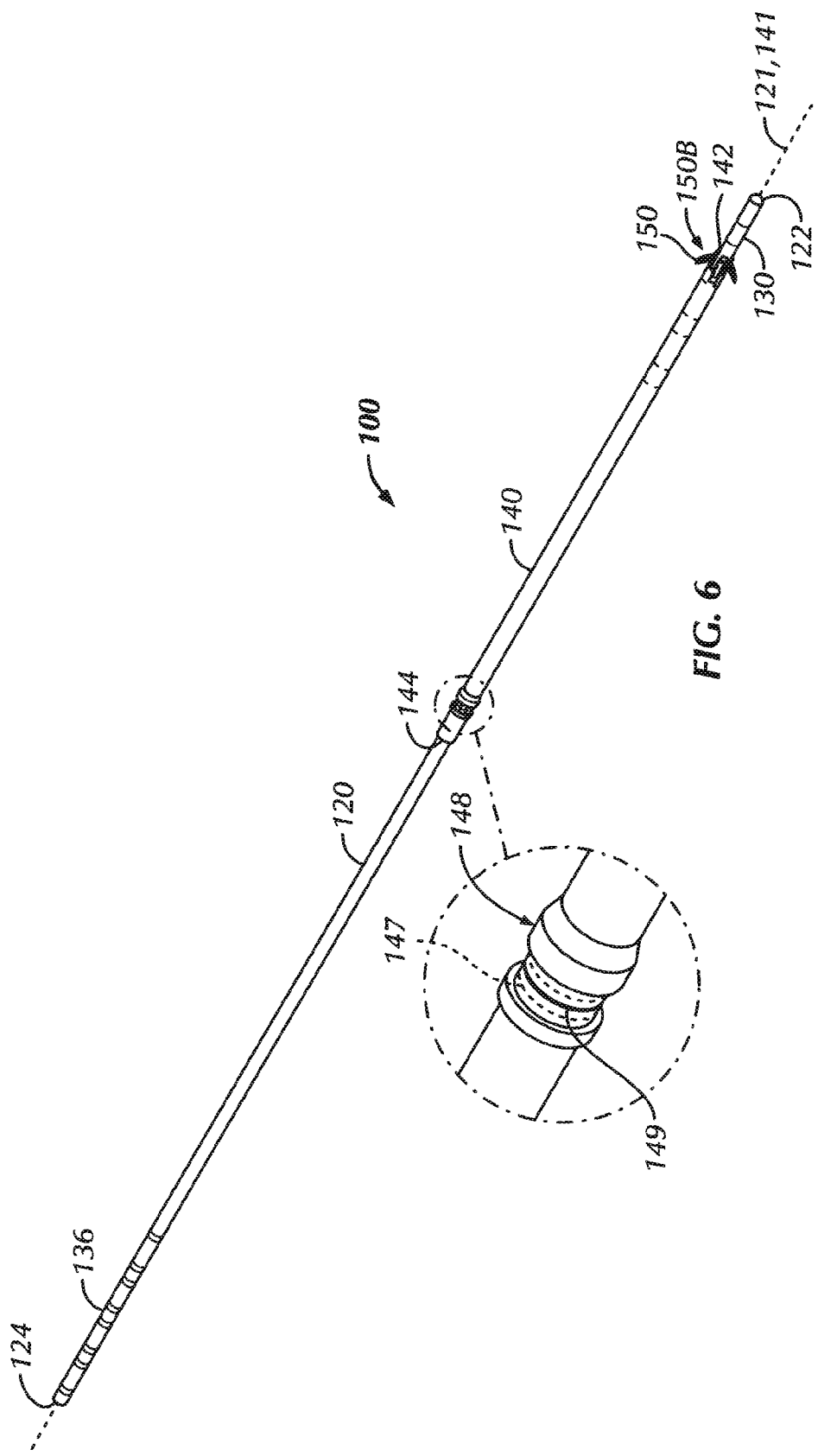
FIG. 6 shows a stimulation lead apparatus with collapsible fixation members in accordance with at least one example of the invention.
Figure 7:
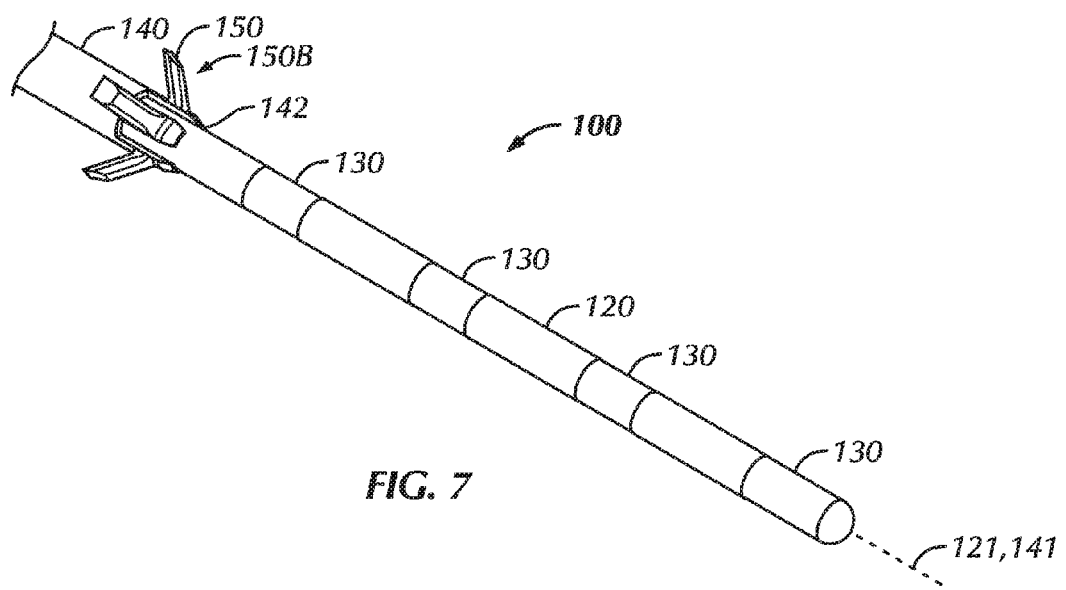
FIG. 7 shows an enlarged view of a distal end of the stimulation lead apparatus of FIG. 6.
Figure 8:
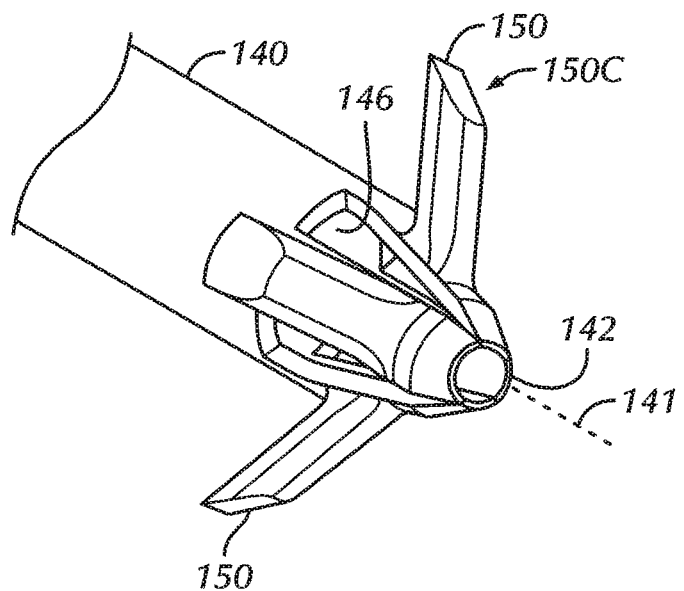
FIG. 8 shows a distal end of a sheath of the stimulation lead apparatus of FIG. 6, the sheath including fixation members during removal of the sheath.

Referring to FIGS. 6 and 7, in some embodiments, a stimulation lead 100 for at least partial implantation within a patient. In some examples, the stimulation lead 100 is configured to stimulate a nerve or other tissue of the patient. In further examples, the stimulation lead 100 is configured to stimulate one or more nerves including, but not limited to a sacral nerve and/or a pudendal nerve of the patient.

In some examples, the stimulation lead 100 includes an elongate lead body 120 including a distal end 122 and a proximal end 124. In some examples, the lead body 120 includes a longitudinal lead axis 121. The lead body 120, in some examples, includes one or more electrodes 130 for stimulating tissue. In some examples, the one or more electrodes 130 are disposed proximate the distal end of the lead body 120. In some examples, the lead body 120 includes four electrodes 130. However, it should be understood that, in other examples, the lead body includes more or fewer than four electrodes depending upon the anatomy of the patient and/or the particular nerve or other tissue that is intended to be stimulated using the stimulation lead. The one or more contacts 136, in some examples, are equal in number to the total number of electrodes 130 on the stimulation lead 100. In some examples, the stimulation lead 100 includes conductors running between the one or more contacts 136 and the corresponding one or more electrodes 130 to electrically couple the one or more electrodes 130 to the one or more contacts 136. In some examples, the lead body 120 includes one or more contacts 136 configured to electrically couple to a pulse generator or other medical device or a lead extension. In some examples, the one or more contacts 136 are configured to electrically couple the one or more electrodes 130 to the pulse generator to transmit electrical stimulation pulses generated by the pulse generator to the appropriate one or more electrodes 130 and, in turn, to the appropriate one or more target nerves and/or target tissues.

Figure 5:
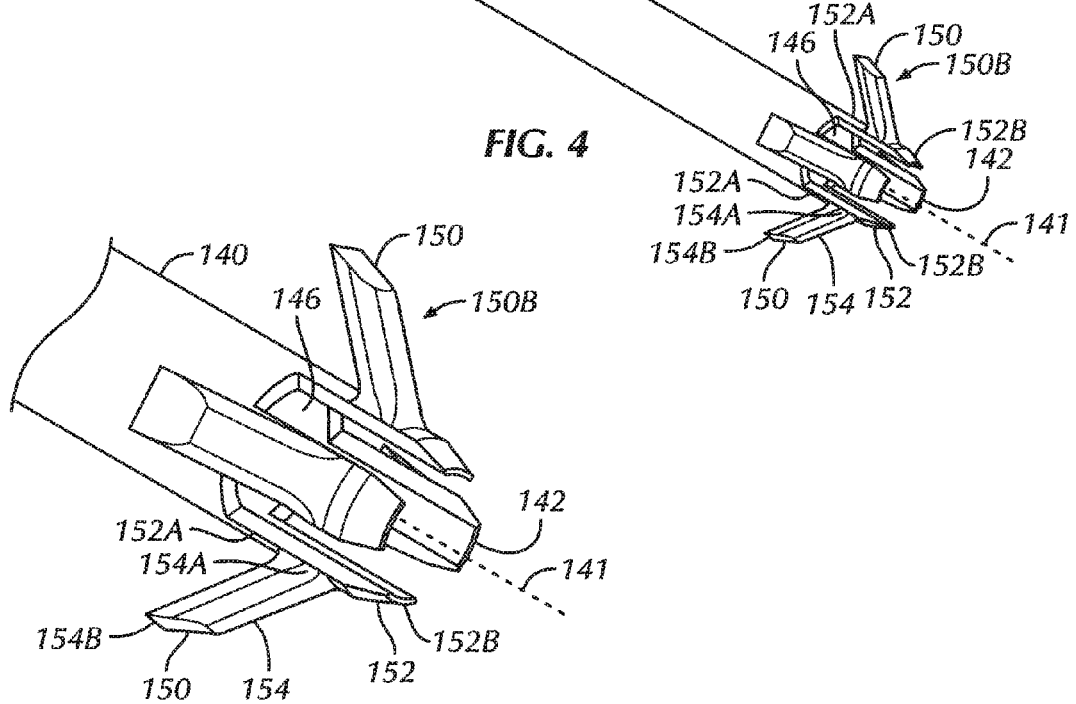
FIG. 5 shows the sheath of FIG. 3, the sheath including fixation members in a deployed configuration.

Referring now to FIGS. 5-7, in some examples, the stimulation lead 100 includes a sheath 140 selectively attachable to the lead body 120. In some examples, the sheath 140 includes a longitudinal sheath axis 141. The sheath 140 includes, in some examples, a lumen 146 extending from a proximal sheath end 144 to a distal sheath end 142. In some examples, the lumen 146 is sized and shaped to accept at least a portion of the lead body 120 within the lumen 146. In some examples, the sheath 140 includes at least one fixation member 150 disposed on the sheath 140. In some examples, the at least one fixation member 150 is configured to at least partially anchor the stimulation lead 100 within the patient. In some examples, the sheath 140 includes a plurality of fixation members 150. In the example shown in FIGS. 5-7, the sheath 140 includes four fixation members 150. In other examples, it is contemplated that the sheath include more or less than four fixation members, provided that the number of fixation members is sufficient to at least partially anchor the stimulation lead within the patient. In some examples, the at least one fixation member 150 is disposed proximate the distal sheath end 142. In some examples, the at least one fixation member 150 includes a tine 154. In other examples, the at least one fixation member 150 includes other fixation members, such as fins, barbs, coils, or the like. It is noted that, in various examples, different numbers, sizes, and/or types of fixation structures can be used with the stimulation lead 100, for instance to adjust or tune fixation of the stimulation lead 100 within the patient. In some examples, the at least one fixation member 150 provides main anchoring (major fixation) of the stimulation lead 100.

In some examples, the sheath 140 is selectively attachable to the lead body 120. That is, in some examples, the sheath 140 can be substantially fixed with respect to the lead body 120. In this way, in some examples, the sheath 140 can be attached to the lead body 120 when the lead body 120 is in a desired location with respect to the patient to allow the at least one fixation member 150 to at least partially anchor the lead body 120 and, in turn, the stimulation lead 100, in place with respect to the patient. In some examples, the sheath 140 is compressively attachable to the lead body 120. In some examples, the sheath 140 includes a suture 149 disposed around the sheath 140, wherein tightening of the suture 149 compressively engages the sheath 140 to the lead body 120. In some examples, the sheath 140 includes a suture groove 148 for retaining the suture 149 within the suture groove 148. In some examples, the suture groove 148 inhibits the suture 149 from migrating along the sheath 140 and/or the lead body 120, for instance, during implantation, which could potentially lead to migration and/or dislodgement of the lead body 120. In some examples, the suture groove 148 is disposed around the sheath 140 proximate a proximal end 144 of the sheath 140. In other examples, the suture groove 148 is disposed around the sheath 140 at a location other than proximate the proximal end 144 of the sheath 140. In some examples, the sheath 140 includes a radiopaque marker 147 proximate the suture groove 148. In various examples, the suture groove 148 or other suture location (or the suture 149 itself) can be marked with a band or other marker including various materials, including, but not limited to barium sulfate, platinum iridium, tungsten, etc. In some examples, the radiopaque marker 147 facilitates a physician or other caregiver in finding the suture 149 (for instance, using fluoroscopy) while the stimulation lead 100 is implanted within the patient, for instance, in order to remove the suture 149 for removal of the lead body 120 and/or the sheath 140 from within the patient, as is described herein. In some examples, the suture 149 and/or suture groove 148 includes material to make the suture 149 and/or suture groove 148 imageable in other imagining modalities in addition to or instead of fluoroscopy, including, but not limited to, one or more of magnetic resonance imaging, computed tomography scanning, ultrasound imaging, or the like. In some examples, the suture groove 148 is integrally formed with the sheath 140. In other examples, the suture groove is disposed in a separate component, such as, but not limited to, a suture sleeve. In still other examples, the sheath 140 can be selectively attached to the lead body 120 using another attachment device, such as, but not limited to, a compression or crimp sleeve, a threaded engagement between the sheath and the lead body, a staple or other fastener, or a combination thereof.

In some examples, with the sheath 140 attached to the lead body 120, the lead body 120 is disposed at least partially within the lumen 146 of the sheath 140. In some examples, the lead body 120 and the sheath 140 are substantially coaxial with the sheath 140 attached to the lead body 120. That is, in some examples, the longitudinal lead axis 121 and the longitudinal sheath axis 141 are substantially collinear with the sheath 140 attached to the lead body 120.

Referring now to FIGS. 3-8, the at least one fixation member 150 includes various configurations. In some examples, the at least one fixation member 150 includes a retracted configuration 150A (FIG. 3) in which the at least one fixation member 150 is disposed proximate the sheath 140 to inhibit the at least one fixation member 150 from engaging with tissue of the patient and anchoring the sheath 140. In this way, in some examples, while the at least one fixation member 150 is in the retracted configuration 150A, the sheath 140 can be moved and manipulated within the patient under the desired location of the sheath 140 is determined and achieved.

In some examples, the at least one fixation member 150 includes a deployed configuration 150B (FIGS. 4-7) in which the at least one fixation member 150 extends radially outwardly from the sheath 140 to engage with the tissue of the patient in order to anchor the stimulation lead 100 within the patient. In some examples, the at least one fixation member 150 extends outwardly from the sheath 140 farther in the deployed configuration 150B than in the retracted configuration 150A. In examples in which the at least one fixation member 150 includes the tine 154, the tine 154 includes a fixed end 154A attached to the sheath 140 and a free end 154B, the free end 154B being spaced radially outwardly from the sheath 140 a greater distance in the deployed configuration 150B than in the retracted configuration 150A. In some examples, the at least one fixation member 150 is biased to the deployed configuration 150B.

In some examples, the at least one fixation member 150 includes a removal configuration 150C (FIG. 8) in which the at least one fixation member 150 is radially inwardly collapsible toward the longitudinal sheath axis 141 with the lead body 120 removed from within the sheath 140. In some examples, the sheath 140 includes at least one base 152 on which the at least one fixation structure 150 is disposed. In some examples, the base 152 is deflectable with respect to the remainder of the sheath 140. In some examples, the base 152 is cantilevered from the sheath 140 and deflectable along a portion proximate a fixed end 152A of the base 152 that is connected to the sheath 140 to allow a free end 152B of the base 152 to rotate inwardly with respect to the sheath 140 toward the longitudinal sheath axis 141. In some examples, the at least one fixation member 150 is retained in the deployed configuration 150B with the lead body 120 disposed within the lumen 146 and extending from the distal end 142 of the sheath 140. With the lead body 120 disposed within the sheath 140, in some examples, the base 152 abuts the lead body 120 and is inhibited from deflecting and allowing the at least one fixation member from moving to the removal configuration 150C. However, in some examples, with the lead body 120 removed from within the sheath 140, the base 152 is able to deflect radially inwardly toward the longitudinal sheath axis 141 to allow the at least one fixation member 150 to be radially inwardly collapsible in the removal configuration 150C. That is, with the lead body 120 removed from within the sheath 140, the at least one fixation member 150 is able to collapse into the now-open area within the sheath 140, thereby allowing the at least one fixation member 150 to fold distally with respect to the sheath 140 with proximal movement of the sheath 140 (for instance, as would occur with a proximally directed force applied to the sheath 140 during removal of the sheath 140 from a patient). In this way, in some examples, removal of the sheath 140 from within the patient is facilitated by decreasing the amount of force for removing the sheath 140 compared to, for instance, another lead having non-collapsible tines.

Figure 4:
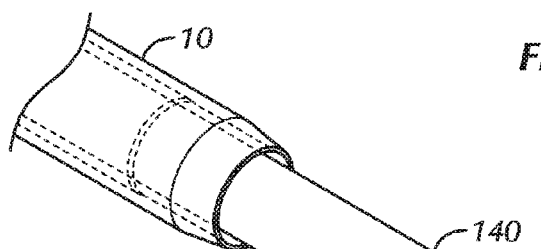
FIG. 4 shows the sheath of FIG. 3 with the introducer moved proximally with respect to the sheath, the sheath including fixation members in a deployed configuration.

Referring now to FIGS. 1-4, one or more components can be used to implant the sheath 140. For instance, in some examples, a tubular introducer 10 or other delivery system or apparatus can be used to retain the sheath 140 during implantation of the sheath 140. In some examples, the introducer 10 includes an open distal end 12, sized to allow distal exiting of the sheath 140 and/or the lead body 120 through the distal end 12. In some examples, the introducer 10 includes a proximal handle 14 to facilitate maneuvering of the introducer, for instance during implantation of the sheath 140. In some examples, the at least one fixation member 150 is retained within the retracted configuration 150A with the at least one fixation member 150 disposed within the introducer 10 to facilitate implantation of the sheath 140, for instance, by inhibiting the at least one fixation member 150 from deploying and/or otherwise engaging with tissue during implantation of the sheath 140. In some examples, removal of the sheath 140 from within the introducer 10 allows the at least one fixation member 150 to move to the deployed configuration 150B (FIG. 4). In some examples, movement of the at least one fixation member 150 to the deployed configuration 150B is facilitated because the at least one fixation member 150 is biased to the deployed configuration 150B.

Figure 1:
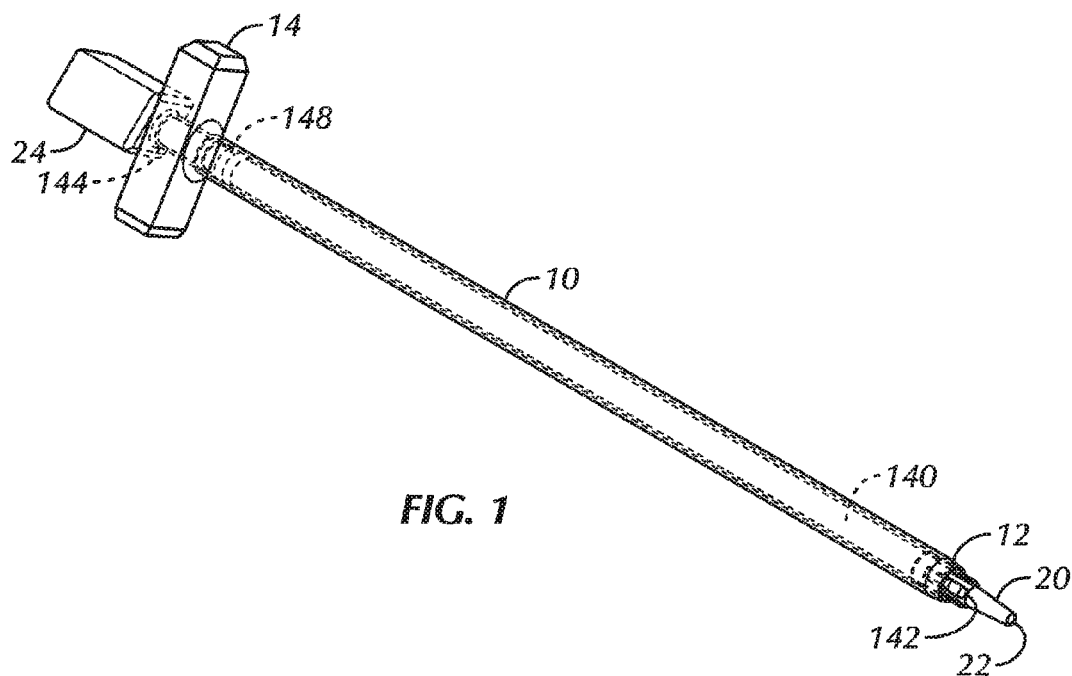
FIG. 1 shows a system for introducing a stimulation lead apparatus with collapsible fixation members in accordance with at least one example of the invention.
Figure 2:
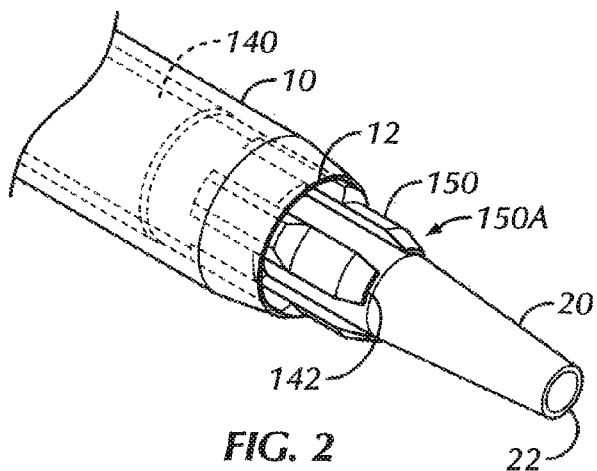
FIG. 2 shows an enlarged view of a distal end of the system of FIG. 1.
Figure 3:
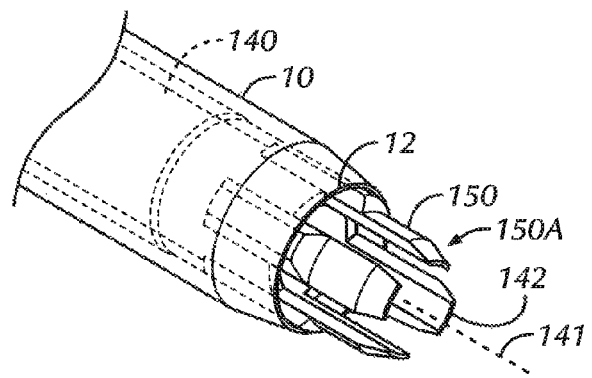
FIG. 3 shows the distal end of the system of FIG. 1 with an obturator removed from within a sheath of the stimulation lead apparatus, the sheath including fixation members in a retracted configuration.

Referring to FIGS. 1 and 2, in some examples, an obturator 20 can be used with the sheath 140 for implantation of the sheath 140 within the patient. In some examples, the obturator 20 includes a distal end 22 configured to extend distally beyond the distal end 12 of the introducer 10 and/or the distal end 142 of the sheath 140. In some examples, the distal end 22 of the obturator 20 is tapered with an atraumatic tip to facilitate insertion of the obturator 20, the sheath 140, and the introducer 10 within the patient and inhibit tissue damage. The obturator 20 can be used within the sheath 140, in some examples, to assist in extending the sheath 140 from the introducer 10, maintaining the at least one fixation member 150 in position, and/or positioning the sheath 140 within the patient. In some examples, the obturator 20 includes a proximal handle 24, for instance, to facilitate removal of the obturator 20 from within the sheath 140. In some examples, once the sheath 140 is positioned in the desired location within the patient, the obturator 20 can be removed from within the sheath 140, thereby allowing for the lead body 120 to be inserted into the sheath 140.

Figure 9:
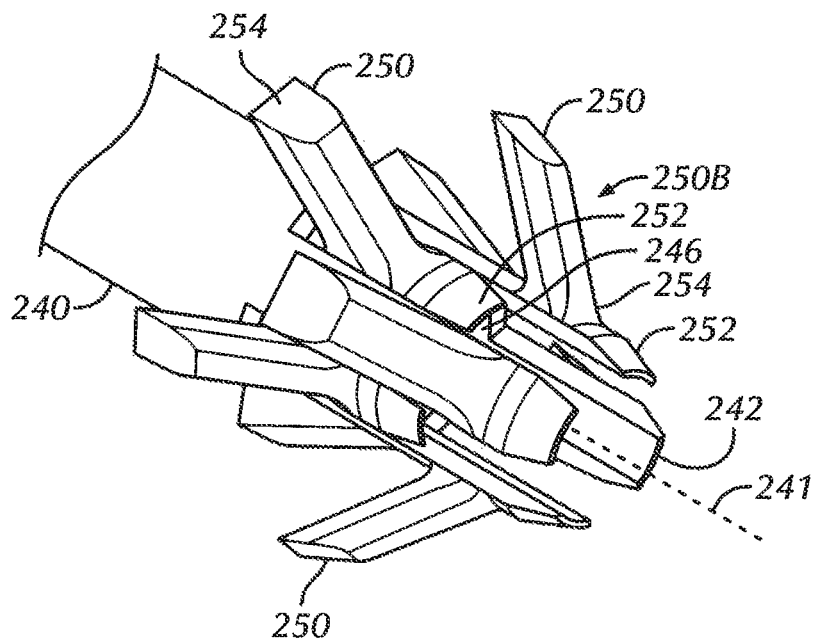
FIG. 9 shows a sheath of a stimulation lead apparatus in accordance with at least one example of the invention, the sheath including fixation members in a deployed configuration.

Referring to FIG. 9, in some examples, a sheath 240 configured differently from the sheath 140 described herein, can be used with the lead body 120 to at least partially anchor the lead body 120 within the patient. In some examples, the sheath 240 is selectively attachable to the lead body 120. In some examples, the sheath 240 includes a longitudinal sheath axis 241. The sheath 240 includes, in some examples, a lumen 246 extending from a proximal sheath end to a distal sheath end 242. In some examples, the lumen 246 is sized and shaped to accept at least a portion of the lead body 120 within the lumen 246. In some examples, the sheath 240 includes at least one fixation member 250 disposed on the sheath 240. In some examples, the at least one fixation member 250 is configured to at least partially anchor the stimulation lead within the patient. In some examples, the sheath 240 includes a plurality of fixation members 250. In the example shown in FIG. 9, the sheath 240 includes two sets of four fixation members 250. In other examples, it is contemplated that the sheath include more or less than eight total fixation members, provided that the number of fixation members is sufficient to at least partially anchor the stimulation lead within the patient. In some examples, the at least one fixation member 250 is disposed proximate the distal sheath end 242. In some examples, the at least one fixation member 250 includes a tine 254. In other examples, the at least one fixation member 250 includes other fixation members, such as fins, barbs, coils, or the like. In some examples, the at least one fixation member 250 includes a deflectable base 252 on which the tine 254 or other fixation member 250 is disposed. As such, similar to the at least one fixation member 150 described herein, the at least one fixation member 250 can include a retracted configuration, a deployed configuration 250B, and a removal configuration. It is noted that, in various examples, different numbers, sizes, and/or types of fixation structures can be used with the stimulation lead, for instance to adjust or tune fixation of the stimulation lead within the patient. In some examples, the at least one fixation member 250 provides main anchoring (major fixation) of the stimulation lead.

In some examples, the sheath 240 differs from the sheath 140 described herein in that the sheath 240 includes a different configuration of fixation members 250. For instance, in the example shown in FIG. 9, the sheath 240 includes two sets of four fixation members 250 disposed proximate the distal sheath end 242. Such a configuration, in some examples, can offer different characteristics, such as, for instance, anchoring strength, than another sheath, such as, but not limited to the sheath 140 described herein. Although only the sheaths 140, 240 are shown and described herein, it should be understood that other configurations of sheaths and/or other configurations of fixation members are contemplated herein. For instance, in various examples, a sheath can include one or more of the following: a different numbers of fixation members, one or more fixation members disposed in a location along the sheath other than at the distal end of the sheath, one or more differently shaped fixation members, two or more fixation members disposed on a base, or the like. In this way, various sheaths can be used or chosen between in order to impart the desired one or more fixation characteristics to the stimulation lead based upon various factors including, but not limited to patient size and/or anatomy, tissue or nerve to be stimulated, or the like.

Referring to FIGS. 1-7, in some examples, the stimulation lead 100 can be implanted within the patient. In some examples, the sheath 140 can be inserted within the introducer 10 for insertion within the patient at a desired implant site. The following description references only the sheath 140 for the sake of convenience; however, it should be understood that the physician or other caregiver can use the sheath 240 or another differently-configured sheath instead of the sheath 140, depending upon the one or more fixation characteristics desired for the particular patient.

In some examples, the obturator 20 can be inserted within the sheath 140 and the introducer 10 to facilitate insertion of the sheath 140 within the patient. In other examples, the introducer 10 can be inserted alone (or with the obturator 20), and, when in the desired location within the patient, the obturator 20 can be removed and the sheath 140 can be passed through the introducer 10 (or the sheath 140 can be passed over the obturator 20 if the obturator 20 is kept within the introducer 10). Once the sheath 140 is disposed in the desired location within the patient, the introducer 10 can be retracted (for instance, pulled proximally from) the sheath 140, allowing the one or more fixation members 150 to move from the retracted configuration 150A to the deployed configuration 150B. In some examples, the lead body 120 can be placed within the lumen 146 of the sheath 140 and extended distally from the distal sheath end 142 to expose at least one of the one or more electrodes 130 of the lead body 120. In some examples, the sheath can be retained within the introducer 10 and the one or more fixation members 150 retained in the retracted configuration 150A and the lead body 120 can be placed within the lumen 146 of the sheath 140 and extended distally from the distal sheath end 142 to expose at least one of the one or more electrodes 130 of the lead body 120, for instance, to perform test stimulations to aid in positioning the stimulation lead 100 before the one or more fixation members 150 are deployed and the stimulation lead 100 is anchored.

Once the sheath 140 and the lead body 120 are in the desired location within the patient and the introducer 10 is removed, the sheath 140 and the lead body 120 can be engaged to one another to inhibit relative motion between the sheath 140 and the lead body 120. In some examples, the sheath 140 and the lead body 120 can be engaged by tightening the suture 149. In some further examples, the suture 149 is disposed within the suture groove 148. In other examples, an attachment device other than or in addition to the suture 149 can be used to engaged and inhibit relative motion between the sheath 140 and the lead body 120.

In some examples, if it is desired to extract the stimulation lead 100, the lead body 120 can be removed from within the sheath 140, leaving the sheath 140 empty and allowing the one or more fixation members 150 to move to the removal configuration 150C, allowing the one or more fixation members 150 to collapse toward the longitudinal sheath axis 141 and into the now-empty lumen 146 of the sheath 140. With the one or more fixation members 150 in the removal configuration 150C, in some examples, the removal force to extract the sheath 140 from the patient is less than that of leads or other devices having non-collapsible tines. In some examples, the removal force for removing the sheath 140 with the one or more fixation members 150 is significantly lower than that of leads or other devices having non-collapsible tines.

In some examples, if the suture 149 is holding the sheath 140 and the lead body 120 together within the patient, the suture 149 must first be removed in order to remove the lead body 120 from within the sheath 140 and ultimately remove the sheath 140 from the patient. Finding the suture location can sometimes be difficult because it is disposed within the patient. In some examples, the suture groove 148 or other location of the suture 149 (or the suture 149 itself) can be marked with the radiopaque material 147 so that it shows up in fluoroscopy (or another imaging modality) to aid the physician or other caregiver in finding the location of the suture 149.

In some examples, because the sheath 140, 240 and the lead body 120 are separate, different sheaths 140, 240 can include different fixation member configurations and the physician or other user can select the sheath configuration according to the anatomy, size, shape, etc. of the patient, the structure around where the distal lead end 122 of the lead body 120 is intended to be implanted, the type of lead body 120, or any other factor that could result in one fixation member configuration being better or more appropriate than another configuration. In various examples, spacing of fixation members 150, type of fixation member 150, number of fixation members 150, or the like can be different with different configurations. This allows the physician or other caregiver, in some examples, to select the sheath 140, 240 having the fixation member configuration that the physician or other caregiver wants rather than being forced to use a fixation member configuration that comes with a lead, for instance.

In some examples, because the lead body 120 (and, in turn, the one or more electrodes 130 of the lead body 120) and the sheath 140, 240 are independent, spacing between the one or more fixation members 150 and the one or more electrodes 130 of the lead body 120 is variable and can be configured according to the patient and/or the physician's or other caregiver's preferences prior to the one or more fixation members 150, 250 being placed in the deployed configuration 150B, 250B and/or the sheath 140, 240 being affixed to the lead body 120 (for instance, with a suture).

The present inventors have recognized various advantages of the subject matter described herein. For instance, in some examples, the apparatuses, systems, and methods described herein can be used to provide an implantable stimulation lead including a selectively collapsible fixation member in order to decrease removal force for removing the stimulation lead from within a patient. By decreasing the removal force, the present inventors have recognized, among other things, that, in some examples, fewer leads will break during removal procedures, potentially leading to decreased complications and cost associated with removal procedures. While various advantages of the example apparatuses, systems, and methods are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A stimulation lead for at least partial implantation within a patient, the stimulation lead comprising:
an elongate lead body including a distal end and a proximal end; and
a sheath selectively attachable to the lead body, the sheath including:
a longitudinal sheath axis;
a lumen extending from a proximal sheath end to a distal sheath end; and a fixation member disposed on the sheath;
wherein, with the sheath attached to the lead body:
the lead body is disposed at least partially within the lumen of the sheath; and
the lead body and the sheath are substantially coaxial;
wherein the fixation member includes:
a retracted configuration in which the fixation member is disposed proximate the sheath;
a deployed configuration in which the fixation member extends radially outwardly from the sheath to anchor the stimulation lead within the patient; and
a removal configuration in which the fixation member is radially inwardly collapsible toward the longitudinal sheath axis with the lead body removed from within the sheath, the removal configuration being different from the retracted configuration and the deployed configuration.

2. The stimulation lead of claim 1, wherein the sheath includes a plurality of fixation members.

3. The stimulation lead of claim 1, wherein the fixation member is disposed proximate the distal sheath end.

4. The stimulation lead of claim 1, wherein the sheath is compressively attachable to the lead body.

5. The stimulation lead of claim 4, wherein the sheath includes a suture disposed around the sheath, wherein tightening of the suture compressively engages the sheath to the lead body.

6. The stimulation lead of claim 1, wherein the sheath includes a suture groove for retaining a suture within the suture groove, wherein tightening of the suture compressively engages the sheath to the lead body.

7. The stimulation lead of claim 6, wherein the suture groove is disposed around the sheath proximate a proximal end of the sheath.

8. The stimulation lead of claim 6, wherein the sheath includes a radiopaque marker proximate the suture groove.

9. The stimulation lead of claim 1, wherein the fixation member includes a tine.

10. The stimulation lead of claim 1, wherein the fixation member is retained within the retracted configuration with the fixation member disposed within an introducer.

11. The stimulation lead of claim 1, wherein the fixation member is retained in the deployed configuration with the lead body disposed within the lumen and extending from the distal end of the sheath.

12. The stimulation lead of claim 1, wherein the fixation member is biased to the deployed configuration.

13. The stimulation lead of claim 1, wherein the sheath includes a base on which the fixation member is disposed, the base being deflectable with respect to a remainder of the sheath, wherein:
with the lead body disposed within the sheath, the base is inhibited from deflecting; and
with the lead body removed from within the sheath, the base is able to deflect radially inwardly toward the longitudinal sheath axis to allow the fixation member to be radially inwardly collapsible in the removal configuration.

14. An apparatus for at least partial implantation within a patient, the apparatus comprising:
a sheath selectively attachable to a lead body, the sheath including:
a longitudinal sheath axis;
a lumen extending from a proximal sheath end to a distal sheath end;
at least one fixation member disposed on the sheath; and
an elongate lead body including a distal end and a proximal end, the lead body being sized and shaped to fit within the lumen of the sheath, wherein, with the lead body disposed within the sheath, the lead body and the sheath are substantially coaxial, wherein the at least one fixation member includes:
a retracted configuration in which the at least one fixation member is disposed proximate the sheath;
a deployed configuration in which the at least one fixation member extends radially outwardly from the sheath to anchor the apparatus within the patient; and a removal configuration in which the at least one fixation member is radially inwardly collapsible toward the longitudinal sheath axis with the lead body removed from within the sheath, the removal configuration being different from the retracted configuration and the deployed configuration.

15. The apparatus of claim 14, wherein the at least one fixation member is disposed proximate a distal end of the sheath.

16. The apparatus of claim 14, wherein the sheath is compressively attachable to the lead body.

17. The apparatus of claim 16, comprising a suture disposed around the sheath within a suture groove proximate a proximal end of the sheath, wherein tightening of the suture compressively engages the sheath to the lead body.

18. The apparatus of claim 14, comprising an introducer removably disposed around the sheath and the at least one fixation member of the sheath, wherein the at least one fixation member is retained within the retracted configuration with the at least one fixation member disposed within the introducer, wherein removal of the sheath from within the introducer allows the at least one fixation member to move to the deployed configuration.

19. The apparatus of claim 14, wherein the at least one fixation member is biased to the deployed configuration.

20. The apparatus of claim 14, wherein the sheath includes a base on which the at least one fixation member is disposed, the base being deflectable with respect to the remainder of the sheath, wherein:

with the lead body disposed within the sheath, the base is inhibited from deflecting; and with the lead body removed from within the sheath, the base is able to deflect radially inwardly toward the longitudinal sheath axis to allow the at least one fixation member to be radially inwardly collapsible in the removal configuration.

* * * * *